(12) United States Patent
Park et al.

(10) Patent No.: US 9,259,279 B2
(45) Date of Patent: Feb. 16, 2016

(54) FORCE SENSING APPARATUS AND OPERATING METHOD OF FORCE SENSING APPARATUS

(71) Applicant: Samsung Electronics Co., Ltd., Suwon-si (KR)

(72) Inventors: Joonah Park, Hwaseong-si (KR); Hyung Kew Lee, Gunpo-si (KR); Soo Chul Lim, Seoul (KR); Bho Ram Lee, Sungnam-si (KR); Hyun Jeong Lee, Hwaseong-si (KR); Seung Ju Han, Seoul (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 66 days.

(21) Appl. No.: 13/965,491

(22) Filed: Aug. 13, 2013

(65) Prior Publication Data

US 2014/0067123 A1    Mar. 6, 2014

(30) Foreign Application Priority Data

Sep. 4, 2012    (KR) .......................... 10-2012-0097851

(51) Int. Cl.
| | | |
|---|---|---|
| *E05B 65/12* | (2006.01) | |
| *A61B 19/00* | (2006.01) | |
| *G01L 5/16* | (2006.01) | |
| *G01L 1/24* | (2006.01) | |
| *G01L 5/00* | (2006.01) | |

(52) U.S. Cl.
CPC ............. *A61B 19/2203* (2013.01); *G01L 1/246* (2013.01); *G01L 5/009* (2013.01); *G01L 5/16* (2013.01); *A61B 2019/464* (2013.01); *Y10S 901/09* (2013.01)

(58) Field of Classification Search
USPC .......................................................... 385/13
See application file for complete search history.

(56) References Cited

U.S. PATENT DOCUMENTS

| | | | |
|---|---|---|---|
| 5,965,880 A * | 10/1999 | Wolf et al. ............... | 250/231.19 |
| 6,389,187 B1 * | 5/2002 | Greenaway et al. ............ | 385/13 |
| 7,300,450 B2 * | 11/2007 | Vleugels et al. .............. | 606/205 |
| 8,197,418 B2 * | 6/2012 | Lal et al. ........................ | 600/552 |
| 2007/0074584 A1 * | 4/2007 | Talarico et al. .................. | 73/856 |
| 2007/0078484 A1 * | 4/2007 | Talarico et al. ............... | 606/205 |
| 2008/0285909 A1 * | 11/2008 | Younge et al. ................... | 385/13 |
| 2009/0185772 A1 * | 7/2009 | Xia et al. ......................... | 385/13 |
| 2010/0087835 A1 * | 4/2010 | Blumenkranz et al. ........ | 606/130 |
| 2010/0272384 A1 * | 10/2010 | Mueller et al. .................. | 385/13 |
| 2011/0137337 A1 * | 6/2011 | van den Dool et al. ........ | 606/205 |
| 2011/0226066 A1 * | 9/2011 | Anand et al. .................... | 73/777 |

FOREIGN PATENT DOCUMENTS

| | | |
|---|---|---|
| JP | 2005-103056 | 4/2005 |
| KR | 10-2008-0089359 | 10/2008 |
| KR | 10-2011-0047926 | 5/2011 |
| KR | 10-2011-0098027 | 9/2011 |

* cited by examiner

Primary Examiner — Bhavesh V Amin
(74) Attorney, Agent, or Firm — NSIP Law

(57) ABSTRACT

A force sensing apparatus and an operating method of the force sensing apparatus may obtain and provide information about a force applied to an object, thereby enabling control of a force to be applied to manipulate the object.

13 Claims, 13 Drawing Sheets

513

603-1   603-2

603-2   611-1

FORCE SENSING APPARATUS AND OPERATING METHOD OF FORCE SENSING APPARATUS

CROSS-REFERENCE TO RELATED APPLICATIONS

This application claims the priority benefit of Korean Patent Application No. 10-2012-0097851, filed on Sep. 4, 2012, in the Korean Intellectual Property Office, the disclosure of which is incorporated herein by reference.

BACKGROUND

1. Field

The following description relates to technology for obtaining and providing information about a force applied to an object.

2. Description of the Related Art

A surgical method using a surgical robot is increasingly being used. The surgical robot may enable surgery to be performed by controlling a surgical tool that transfers a force to a patient according to manipulation by a surgeon.

The surgical robot may control and utilize the surgical tool and thus, may be suitable for performing a remote surgery on a part of a body. In addition, the surgical robot may aid in preventing hand shaking of the surgeon. Accordingly, the surgical robot may be used for a surgical procedure that requires minute and accurate manipulation, such as prostate cancer surgery, for example.

SUMMARY

The foregoing and/or other aspects are achieved by providing a force sensing apparatus, including n support frames, n sensing units of a first group, each being fixed to the n support frames, respectively, to sense a compressive strain and a tensile strain of each of the n support frames, and a processor to obtain information about a force applied to an object associated with the n support frames, based on data sensed by the n sensing units of the first group.

The processor may obtain at least one of a direction and a magnitude of the force applied to the object, based on the data sensed by the n sensing units of the first group with respect to the compressive strain and the tensile strain of each of the support frames.

When the n sensing units of the first group sense a compressive strain with respect to a number of support frames, among the n support frames, and a tensile strain with respect to all remaining support frames, the processor may obtain at least one of a direction and a magnitude of a force applied to the object in a horizontal direction.

When the n sensing units of the first group sense a compressive strain with respect to all of the n support frames, or when the n sensing units of the first group sense a tensile strain with respect to all of the n support frames, the processor may obtain at least one of a direction and a magnitude of a force applied to the object in a vertical direction.

The apparatus may further include a bottom frame disposed under the n support frames, wherein the bottom frame may include a bottom hole disposed to be perpendicular to the n support frames, and grooves formed at the bottom hole to correspond to the n support frames.

The apparatus may include a first grasper, a second grasper, and an adjusting unit to adjust a pivot angle between the first grasper and the second grasper. In this instance, the processor may obtain at least one of information regarding whether the object is gripped, and a magnitude of a force applied to grip the object, using a compressive strain and a tensile strain of the first grasper and the second grasper.

The apparatus may further include two sensing units of a second group, wherein the two sensing units of the second group may include a first sensing unit fixed to the first grasper to sense a compressive strain and a tensile strain of the first grasper, and a second sensing unit fixed to the second grasper to sense a compressive strain and a tensile strain of the second grasper.

When the two sensing units of the second group sense a tensile strain with respect to both the first grasper and the second grasper, the processor may determine that the object is being gripped with a magnitude of a force that is proportional to the tensile strain.

The apparatus may further include a drive shaft spanning a first side frame including a number of support frames, among the n support frames, and a second side frame including all remaining support frames, excluding the number of the support frames from the first side, the drive shaft being connected to the first grasper and the second grasper.

The foregoing and/or other aspects are achieved by providing an operating method of a force sensing apparatus, the method including sensing a compressive strain and a tensile strain of each of n support frames, using n sensing units of a first group, each being fixed to the n support frames, respectively, and obtaining information about a force applied to an object associated with the n support frames, based on data sensed by the n sensing units of the first group.

The obtaining may include operating at least one of a direction and a magnitude of the force applied to the object, based on the data sensed by the n sensing units of the first group with respect to the compressive strain and the tensile strain of each of the support frames.

The obtaining may include obtaining at least one of a direction and a magnitude of a force applied to the object in a horizontal direction when the n sensing units of the first group sense a compressive strain with respect to a number of support frames, among the n support frames, and a tensile strain with respect to all remaining support frames.

The obtaining may include obtaining at least one of a direction and a magnitude of a force applied to the object in a vertical direction when the n sensing units of the first group sense a compressive strain with respect to all of the n support frames, or when the n sensing units of the first group sense a tensile strain with respect to all of the n support frames.

The method may further include sensing a compressive strain and a tensile strain of a first grasper and a second grasper, using sensing units of a second group, each being fixed to the first grasper and the second grasper, respectively.

The method may further include obtaining at least one of information regarding whether the object is gripped, and a magnitude of a force applied to grip the object, using the compressive strain and the tensile strain of the first grasper and the second grasper.

The obtaining may include determining that the object is being gripped with a magnitude of a force that is proportional to the tensile strain when the sensing units of the second group sense a tensile strain with respect to both the first grasper and the second grasper.

The foregoing and/or other aspects are achieved by providing a system for performing a surgical operation including a surgical apparatus for manipulation of a surgical instrument; a control apparatus to receive a command for control of the surgical apparatus, provide a control signal to the surgical apparatus, and provide feedback from the surgical apparatus; and a force sensing apparatus including a plurality of support frames; a plurality of support frame sensors, each sensor provided on each of the plurality of support frames, respectively, to sense a compressive strain and a tensile strain of each of the plurality of support frames; and a processor to obtain information about a force applied to an object by the plurality of support frames, based on data sensed by the plurality of support frame sensors.

Additional aspects of embodiments will be set forth in part in the description which follows and, in part, will be apparent from the description, or may be learned by practice of the disclosure.

BRIEF DESCRIPTION OF THE DRAWINGS

These and/or other aspects will become apparent and more readily appreciated from the following description of embodiments, taken in conjunction with the accompanying drawings of which.

DETAILED DESCRIPTION

Figure 1:
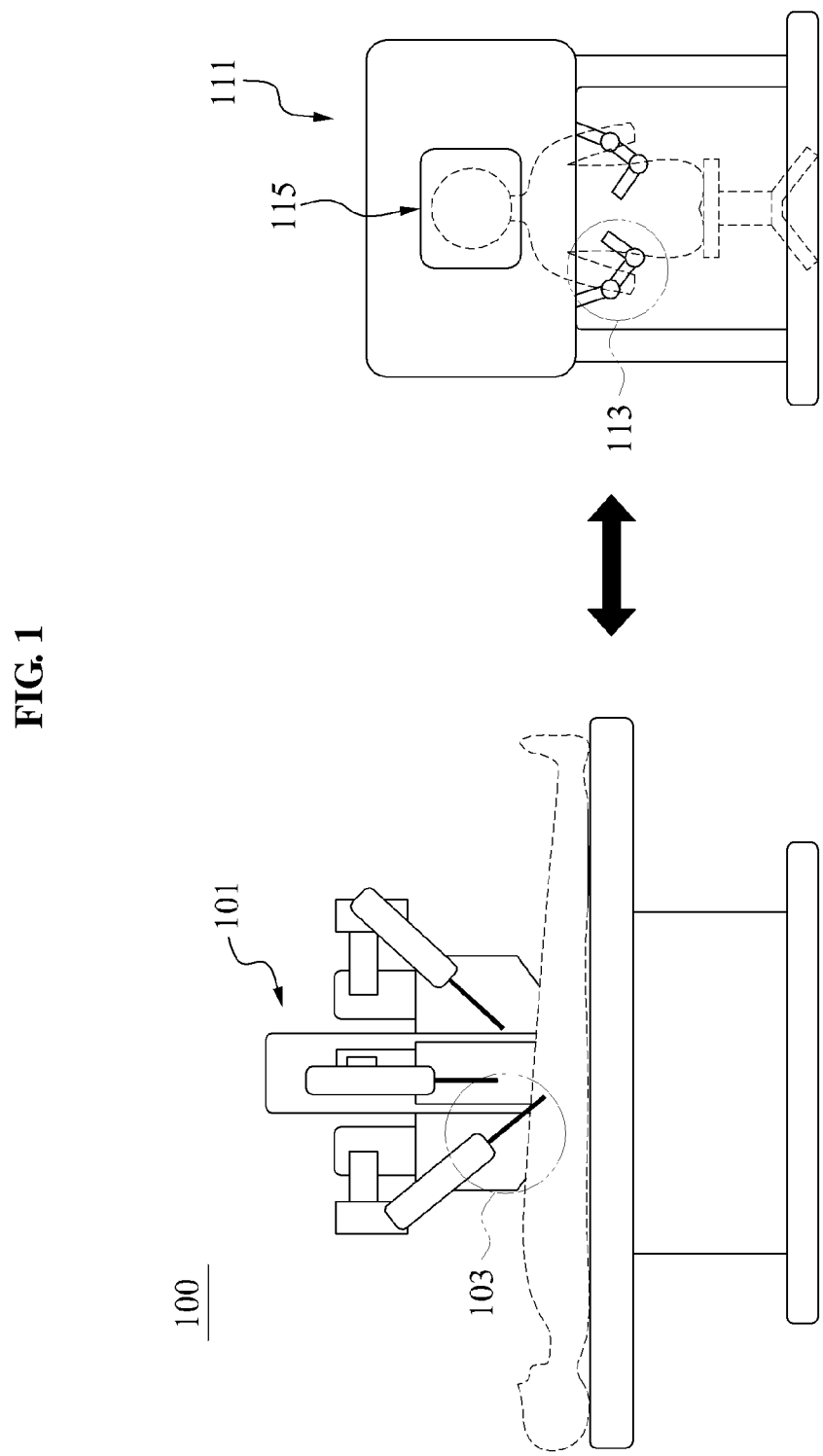
FIG. 1 illustrates medical equipment using a force sensing apparatus according to example embodiments.

Reference will now be made in detail to embodiments, examples of which are illustrated in the accompanying drawings, wherein like reference numerals refer to like elements throughout. Embodiments are described below to explain the present disclosure by referring to the figures.

FIG. 1 illustrates medical equipment 100 using a force sensing apparatus 103 according to example embodiments.

Referring to FIG. 1, the medical equipment 100 may include a surgical apparatus 101, and a control apparatus 111.

The surgical apparatus 101 may correspond to, for example, a slave robot. The surgical apparatus 101 may transfer a force to an object, for example, a human tissue or an organ, using the force sensing apparatus 103 provided as a surgical instrument. In this instance, the surgical apparatus 101 may receive, through a wire or by wireless communication, for example, a strain signal associated with a strain of the object or a grip signal associated with a grip of the object that may be generated by the control apparatus 111. The surgical apparatus 101 may operate the force sensing apparatus 103 based on the received signal, thereby gripping the object or applying a force to the object.

The surgical apparatus 101 may obtain information about a force applied to the object, through the force sensing apparatus 103, and may provide the obtained information to the control apparatus 111 such that the control apparatus 111 may verify the actual force applied to the object. Here, the information about the force transferred to the object may include, for example, information about a force applied to the object or information about a force applied to grip the object, for example. In this instance, the force sensing apparatus 103 may readily obtain the information about the force transferred to the object, using data sensed by n sensing units of a first group and sensing units of a second group. The n sensing units of the first group may be included in a body frame that may be strained in at least one direction, and may be referred to as frame sensors. The sensing units of the second group may be included in a first grasper and a second grasper that are disposed in an upper portion of the body frame to be in contact with the object, and may be referred to as grasper sensors.

The control apparatus 111 may correspond to, for example, a master controller. The control apparatus 111 may generate a strain signal associated with a strain of the object or a grip signal associated with a grip of the object, based on a force input from a finger of a user, for example, a surgeon, using a force controlling apparatus 113. The control apparatus 111 may provide the generated signal to the surgical apparatus 101 through a wire or through wireless communication, for example.

In addition, the control apparatus 111 may display the information about the force fed back from the surgical apparatus 101, on a display unit 115. Accordingly, the force actually transferred to the object may be readily verified, and a force controlled by the user may be minutely controlled based on the verified force.

Figure 2:
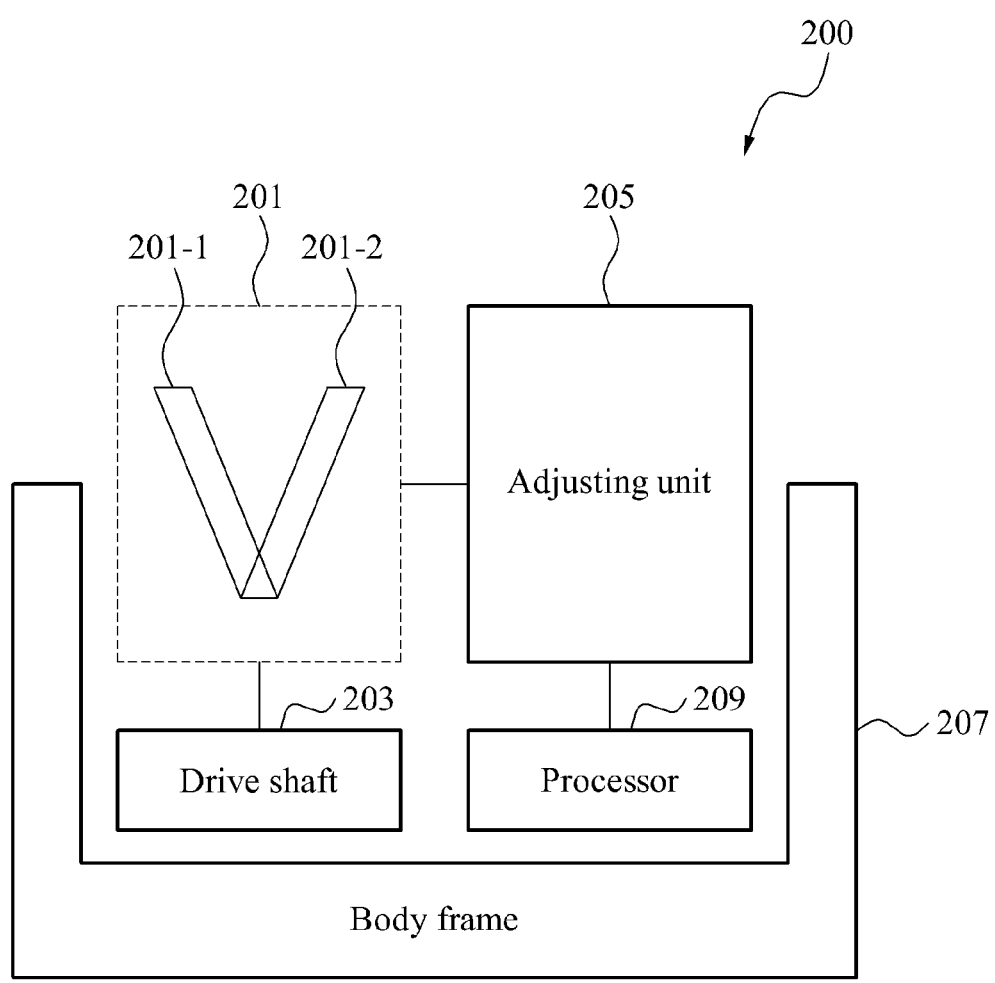
FIG. 2 illustrates a configuration of a force sensing apparatus according to example embodiments.

FIG. 2 illustrates a configuration of a force sensing apparatus 200 according to example embodiments.

Referring to FIG. 2, the force sensing apparatus 200 may include graspers 201, a drive shaft 203, an adjusting unit 205, a body frame 207, and a processor 209.

The graspers 201 may include a first grasper 201-1 and a second grasper 201-2. However, the disclosure is not limited to the above. For example, only a single grasper, such as a hooked instrument, or an additional third grasper, may be provided as appropriate. The graspers 201 may grip an object, based on adjustment of a pivot angle between the first grasper 201-1 and the second grasper 201-2. Here, the pivot angle may refer to an extent by which the first grasper 201-1 and the second grasper 201-2 are splayed, based on a point at which the first grasper 201-1 intersects the second grasper, for example, the drive shaft 203 connecting the first grasper 201-1 and the second grasper 201-2.

The first grasper 201-1 and the second grasper 201-2 may include sensing units of a second group to sense a strain of the first grasper 201-1 and the second grasper 201-2, respectively. For example, the first grasper 201-1 may include a first sensing unit, among the sensing units of the second group. The second grasper 201-2 may include a second sensing unit, among the sensing units of the second group. A sensing unit of the second group included in each of the first grasper 201-1 and the second grasper 201-2 may include, for example, an optical fiber Bragg grating (FBG) or an optical strain gauge. However, the disclosure is not limited to these types of sensing units, and any sensing unit to detect a force applied may be used as appropriate. The sensing unit of the second group may sense a tensile strain or a compressive strain of the first grasper 201-1 and the second grasper 201-2.

The drive shaft 203 may penetrate a first connection hole of the first grasper 201-1 and a second connection hole of the second grasper 201-2, thereby connecting the first grasper 201-1 and the second grasper 201-2. Here, the drive shaft 203 may penetrate the first connection hole and the second connection hole, each disposed at a point at which the first grasper 201-1 intersects the second grasper 201-2, and may connect the first grasper 201-1 and the second grasper 201-2. In this instance, the drive shaft 203 may enable rotation of the first grasper 201-1 and the second grasper 201-2 such that a pivot angle may be changed.

In addition, the drive shaft 203 may span a first side frame and a second side frame within the body frame 207, and may be connected to the first grasper 201-1 and the second grasper 201-2. Here, the first side frame may include a number of support frames, among the n support frames. The second side frame may include all remaining support frames, excluding the number of the support frames from the first side frames. For example, the drive shaft 203 penetrating the first connection hole of the first grasper 201-1 and the second connection hole of the second grasper 201-2 may be inserted into a first connecting hole of the first side frame and a second connecting hole of the second side frame within the body frame 207, thereby connecting the first grasper 201-1 and the second grasper 201-2 to the body frame 207.

The adjusting unit 205 may adjust a pivot angle between the first grasper 201-1 and the second grasper 201-2, based on a grip signal associated with a grip of the object. The adjusting unit 205 may include, for example, an adjusting shaft that is inserted into a first adjusting hole and a second adjusting hole formed in the first grasper 201-1 and the second grasper 201-2, respectively. The adjusting shaft may adjust the pivot angle between the first grasper 201-1 and the second grasper 201-2, by adjusting a position at which the adjusting shaft is inserted into the first adjusting hole and the second adjusting hole, based on the grip signal.

In addition, the adjusting unit 205 may include, for example, a pulley that rotates based on the drive shaft 203. The pulley may adjust the pivot angle between the first grasper 201-1 and the second grasper 201-2, by controlling a rotation direction or a degree of rotation based on the grip signal. However, the disclosure is not limited to the above. For example, any structure appropriate for rotation, such as a gear system, for example, may be provided to rotate the drive shaft.

The body frame 207 may be strained in at least one direction, based on a strain signal associated with a strain of the object. The body frame 207 may include n support frames. Here, n denotes a natural number. For example, the body frame 207 may include four support frames, that is, two support frames included in the first side frame and the two other support frames included in the second side frame.

The n sensing units of the first group, each being provided, such as fixed, inserted, or attached, for example, to the n support frames, respectively, may sense a compressive strain and a tensile strain of each of the n support frames. Here, each of the n sensing units of the first group may include, for example, an optical FBG or an optical strain gauge, similar to a sensing unit of the second group. However, the disclosure is not limited to these types of sensing units, and any sensing unit to detect a force applied may be used as appropriate.

In addition, when the body frame 207 includes the first side frame and the second side frame, each including two support frames, one side of the drive shaft 203 may be inserted into the first connecting hole of the first side frame, and another side of the drive shaft 203 may be inserted into the second connecting hole of the second side frame, such that the body frame 207 may be connected to the first grasper 201-1 and the second grasper 201-2.

The processor 209 may obtain information about a force applied to the object associated with the n support frames, based on data sensed by the n sensing units of the first group. For example, the processor 209 may obtain at least one of a direction and a magnitude of the force applied to the object, through the first grasper 201-1 and the second grasper 201-2, based on a compressive strain, a tensile strain, and/or a change in length of each of the n support frames within the first side frame and the second side frame, the n support frames into which the n sensing units of the first group are inserted.

As an example, the n sensing units of the first group may sense a compressive strain with respect to a number of support frames, among the n support frames, and a tensile strain with respect to all remaining support frames. Here, the number of support frames may correspond to, for example, the support frames within the first side frame. The all remaining support frames may correspond to, for example, the support frames within the second side frame paired with the first side frames. In this instance, the processor 209 may obtain at least one of a direction and a magnitude of a force applied to the object in a horizontal direction. Here, the horizontal direction may refer to, for example, an X-axis direction or a Y-axis direction. The direction of the force applied to the object in the horizontal direction may correspond to, for example, a direction of a force applied from the second side frame to the first side frame.

As an example, when the n sensing units of the first group sense a compressive strain with respect to all of the n support frames, or when the n sensing units of the first group sense a tensile strain with respect to all of the n support frames, the processor 209 may obtain at least one of a direction and a magnitude of a force applied to the object in a vertical direction. Here, all of the n support frames may correspond to, for example, all support frames within the first side frame and the second side frame. In addition, the vertical direction may refer to, for example, a Z-axis direction. For example, when the n sensing units of the first group sense a compressive strain with respect to all of the n support frames, the processor 209 may determine that the force is applied in a down-vertical direction, that is, a negative (−) Z-axis direction. In addition, when the n sensing units of the first group sense a tensile strain with respect to all of the n support frames, the processor 209 may determine that the force is applied in an up-vertical direction, that is, a positive (+) Z-axis direction.

In addition, the processor 209 may obtain information about a force applied to grip the object, through the sensing units of the second group, each fixed to the first grasper 201-1 and the second grasper 201-2, respectively. For example, when the two sensing units of the second group sense a tensile strain with respect to the first grasper 201-1 and the second grasper 201-2, the processor 209 may determine that the object is being gripped with a magnitude of a force that is proportional to the tensile strain.

The processor 209 may provide the information about the force transferred to the object, by outputting the information about the force transferred to the object, through a display unit (not shown), based on the data sensed by the first sensing unit and the second sensing unit. Here, the information about the force transferred to the object may include, for example, information about a force applied to the object, and information about a force applied to grip the object. In this instance, the display unit may be configured to be included in the force sensing apparatus 200. However, the configuration of the display unit may not be limited thereto, and the display unit may be configured to be included in a control apparatus that generates the grip signal or the strain signal.

Figure 3:
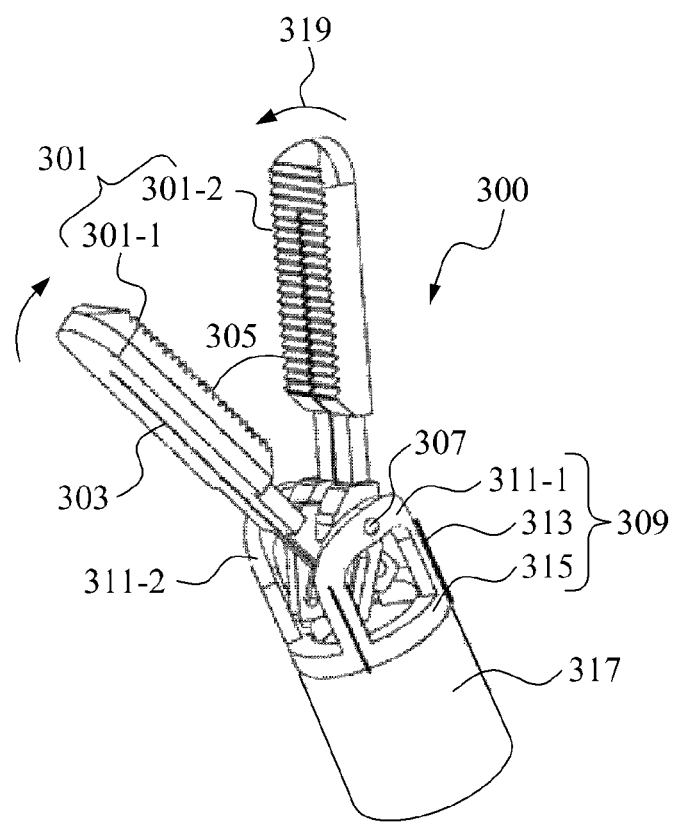
FIG. 3 illustrates a force sensing apparatus according to example embodiments.

FIG. 3 illustrates a force sensing apparatus 300 according to example embodiments.

Referring to FIG. 3, the force sensing apparatus 300 may include graspers 301, a drive shaft 307, an adjusting unit (not shown), a body frame 309, and a tube frame 317.

The graspers 301 may be provided, by way of example, in a form of forceps. The graspers 301 may include a first grasper 301-1 and a second grasper 301-2. The graspers 301 may grip an object based on adjustment of a pivot angle 305 between the first grasper 301-1 and the second grasper 301-2. In this instance, the first grasper 301-1 and the second grasper 301-2 may include projections on surfaces facing each other to prevent the object from slipping when gripping the object.

The first grasper 301-1 and the second grasper 301-2 may include sensing units 303 of a second group to sense a strain of the first grasper 301-1 and the second grasper 301-2, respectively. Here, a first sensing unit fixed to the first grasper 301-1 may sense a compressive strain and a tensile strain of the first grasper 301-1. A second sensing unit fixed to the second grasper 301-2 may sense a compressive strain and a tensile strain of the second grasper 301-1.

A sensing unit 303 of the second group included in each of the first grasper 301-1 and the second grasper 301-2 may include, for example, an optical FBG or an optical strain gauge. Here, the optical FBG may correspond to an optical FBG for measuring temperature which compensates for an interference of a signal caused by a change in temperature.

The drive shaft 307 may penetrate a first connection hole and a second connection hole, each disposed at a point at which the first grasper 301-1 intersects the second grasper 301-2, and may connect the first grasper 301-1 and the second grasper 301-2. In this instance, the drive shaft 307 may enable rotation of the first grasper 301-1 and the second grasper 301-2 such that a pivot angle may be changed.

In addition, the drive shaft 307 penetrating the first connection hole of the first grasper 301-1 and the second connection hole of the second grasper 301-2 may be inserted into a first connecting hole of a first side frame 311-1 and a second connecting hole of a second side frame 311-2 within the body frame 309, thereby connecting the first grasper 301-1 and the second grasper 301-2 to the body frame 309.

The adjusting unit may adjust the pivot angle 305 between the first grasper 301-1 and the second grasper 301-2, based on a grip signal associated with a grip of the object.

The body frame 309 may be strained in at least one direction, based on a strain signal associated with a strain of the object. Here, the body frame 309 may include the first side frame 311-1, the second side frame 311-2, n sensing units 313 of a first group, and a bottom frame 315.

Each of the first side frame 311-1 and the second side frame 311-2 may include a number of support frames, among n support frames. In this instance, each of the first side frame 311-1 and the second side frame 311-2 may include a first hole, and m support frames formed by the first hole. Here, m denotes a natural number. For example, each of the first side frame 311-1 and the second side frame 311-2 may include a first hole, and two support frames formed by the first hole on both sides. Here, when compared to a side frame excluding the first hole, a side frame including the first hole may be self-strained flexible at a relatively low stiffness, thereby enabling minute sensing of a strain of a support frame through the n sensing units 313 of the first group.

Each of the n sensing units 313 of the first group may be fixed to the n support frames within the first side frame 311-1 and the second side frame 311-2, respectively, and may sense a strain of each of the n support frames. For example, the n sensing units 313 of the first group may correspond to a total of four sensing units, for example, two sensing units inserted into two support frames formed on both sides of the first side frame 311-1, and the other two sensing units inserted into the second side frame 311-2 corresponding to the first side frame 311-1, in an identical manner. The four sensing units 313 of the first group may sense a tensile strain or a compressive strain of the four support frames, respectively. Here, each of the n sensing units 313 of the first group may include an optical FBG or an optical strain gauge.

The n sensing units 313 of the first group may be inserted into the first side frame 311-1 and the second side frame 311-2 of the body frame 309. When the n sensing units of the first group are inserted into the tube frame 317, deterioration in sensing performance caused by a frictional force with respect to a trocar that supports the force sensing apparatus 300 may be prevented.

The bottom frame 315 may be disposed under the first side frame 311-1 and the second side frame 311-2, for example, under the n support frames. In particular, the bottom frame 315 may be disposed between the first side frame 311-1 and the second side frame 311-2 and the tube frame 317, and may connect the first side frame 311-1 and the second side frame 311-2 to the tube frame 317. Here, the bottom frame 315 may be disposed to be perpendicular to the n support frames, may include a bottom hole, and may contain grooves formed at the bottom hole to correspond to the n support frames.

The tube frame 317 may be disposed under the bottom frame 315. A wire may be disposed in the tube frame 317 to transfer the grip signal or the strain signal generated by a control apparatus (not shown) to the adjusting unit and the body frame 309 via the bottom hole within the bottom frame 315, respectively.

The force sensing apparatus 300 may further include a processor (not shown). The force sensing apparatus 300 may use the processor to obtain information about a force transferred to the object, and to provide the obtained information to a display unit (not shown). Here, the information about the force transferred to the object may correspond to, for example, information about a force applied to the object, and information about a force applied to grip the object. However, the disclosure is not limited to the above. For example, the processor may be located in the surgical apparatus 101, or the control apparatus 111, such that the force sensing apparatus merely provides sensing data to the processor for processing.

Here, the processor may obtain a direction and a magnitude of the force applied to the object, through the first grasper 301-1 and the second grasper 301-2, using a strain of the support frames within the side frames into which the n sensing units 313 of the first group are inserted. In particular, when the n sensing units 313 of the first group sense a compressive strain with respect to the support frames within the first side frame 311-1, and a tensile strain with respect to the support frames within the second side frame 311-2 paired with the first side frame 311-1, the processor may obtain at least one of a direction and a magnitude of a force applied to the object in a horizontal direction.

In addition, the processor may obtain at least one of information regarding whether the object is gripped, and a magnitude of a force applied to grip the object, using a strain of the first grasper 301-1 and a strain of the second grasper 301-2, the first grasper 301-1 and the second grasper 301-2 including the sensing units 303 of the second group. In particular, when the sensing units 303 of the second group sense a tensile strain with respect to the first grasper 301-1 and the second grasper 301-2, the processor may determine that the object is being gripped with a magnitude of a force that is proportional to the tensile strain. That is, when the pivot angle 305 between the first grasper 301-1 and the second grasper 301-2 is adjusted to grip the object, a reaction with respect to a force 319 may cause a tensile strain on the first grasper 301-1 and the second grasper 301-2 in a direction of an external side. Here, the force 319 may refer to a force applied when the first grasper 301-1 and the second grasper 301-2 face each other.

Figure 4A:
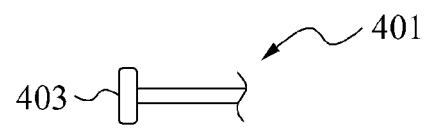
FIGS. 4A through 4C illustrate an adjusting unit in a force sensing apparatus according to example embodiments.
Figure 4B:
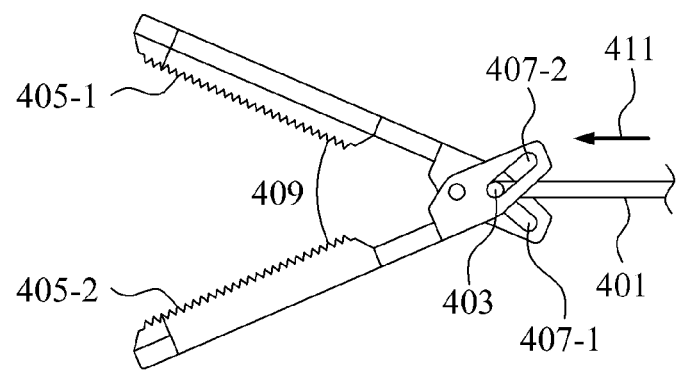
Figure 4C:
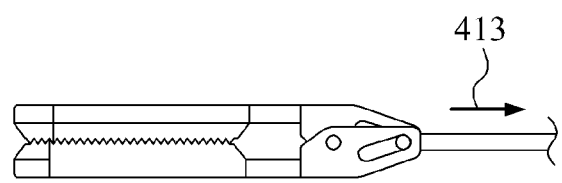

FIGS. 4A through 4C illustrate an adjusting unit in a force sensing apparatus according to example embodiments.

Referring to FIGS. 4A through 4C, the force sensing apparatus may include an adjusting unit to adjust a pivot angle between a first grasper and a second grasper, based on a grip signal associated with a grip of an object.

The adjusting unit may correspond to, for example, a T-shaped adjusting shaft 401. The adjusting shaft 401 may include a protruding portion 403 that protrudes on both sides. The protruding portion 403 may be disposed to be inserted into a first adjusting hole 407-1 and a second adjusting hole 407-2, each formed in a first grasper 405-1 and a second grasper 405-2, respectively. In this instance, the adjusting shaft 401 may move in a predetermined direction, based on the grip signal so as to adjust a position at which the protruding portion 403 is to be inserted into the first adjusting hole 407-1 and the second adjusting hole 407-2, thereby adjusting a pivot angle 409 between the first grasper 405-1 and the second grasper 405-2.

Referring to FIG. 4B, the force sensing apparatus may fully extend the adjusting shaft 401 in a first direction 411 based on the grip signal such that the protruding portion 403 of the adjusting shaft 401 may be moved to a left side of the first adjusting hole 407-1 and the second adjusting hole 407-2. Accordingly, the adjusting shaft 401 may adjust the pivot angle 409 between the first grasper 405-1 and the second grasper 405-2 to a maximum angle, as shown in FIG. 4B.

Referring to FIG. 4C, the force sensing apparatus may fully extend the adjusting shaft 401 in a second direction 413, which may be an opposite direction to direction 411, based on the grip signal, such that the protruding portion 403 of the adjusting shaft 401 may be moved to a right side of the first adjusting hole 407-1 and the second adjusting hole 407-2. Accordingly, the adjusting shaft 401 may adjust the pivot angle 409 between the first grasper 405-1 and the second grasper 405-2 to a minimum angle so that the object may be gripped, as shown in FIG. 4C. Additionally, the angle of the first grasper may be fixed, while the second grasper rotates from a minimum pivot angle to a maximum pivot angle.

Figure 5A:
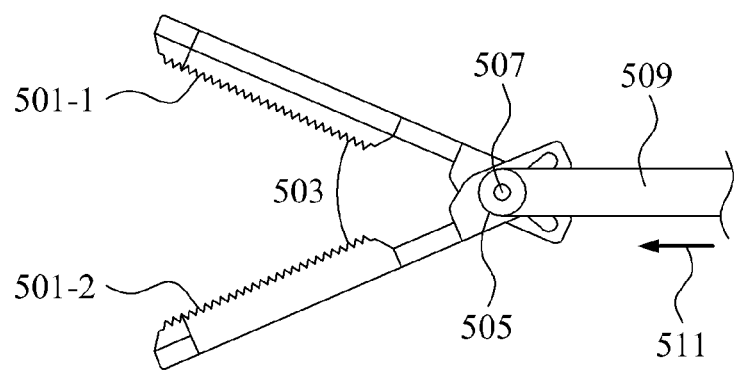
FIGS. 5A and 5B illustrate an adjusting unit in a force sensing apparatus according to other example embodiments.
Figure 5B:
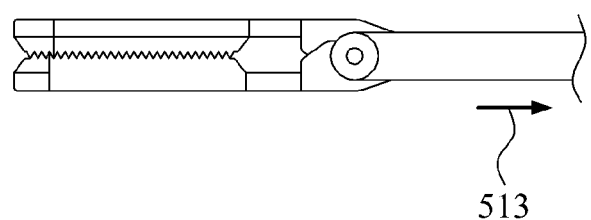

FIGS. 5A and 5B illustrate an adjusting unit in a force sensing apparatus according to other example embodiments.

Referring to FIGS. 5A and 5B, the force sensing apparatus may include the adjusting unit to adjust a pivot angle 503 between a first grasper 501-1 and a second grasper 501-2, based on a grip signal associated with a grip of an object.

The adjusting unit may correspond to, for example, a pulley 505. The adjusting unit may rotate based on a drive shaft 507 to adjust the pivot angle 503 between the first grasper 501-1 and the second grasper 501-2 by controlling a rotation direction or a rotation amount based on the grip signal. Here, the drive shaft 507 may connect the first grasper 501-1 and the second grasper 501-2 to a body frame 509.

Referring to FIG. 5A, the force sensing apparatus may fully rotate the pulley 505 in a first direction 511 based on the grip signal, thereby adjusting the pivot angle 503 between the first grasper 501-1 and the second grasper 501-2 to a maximum angle. In addition, referring to FIG. 5B, the force sensing apparatus may fully rotate the pulley 505 in a second direction 513, which may be an opposite direction to direction 511, based on the grip signal, thereby adjusting the pivot angle 503 between the first grasper 501-1 and the second grasper 501-2 to a minimum angle so that the object may be gripped.

Figure 6A:
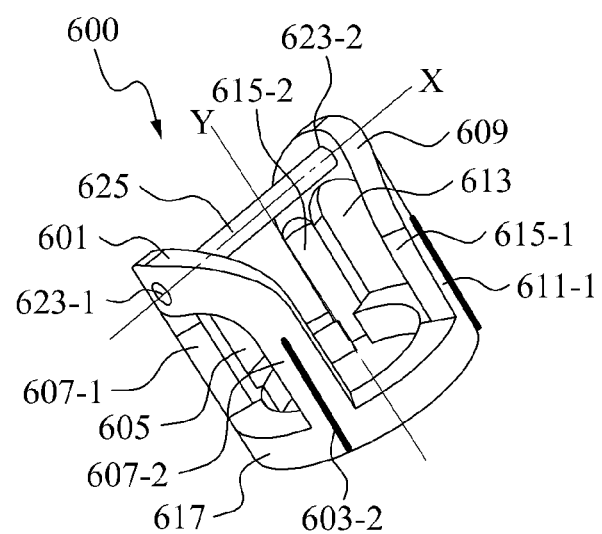
FIGS. 6A through 6D illustrate a body frame in a force sensing apparatus according to example embodiments.
Figure 6B:
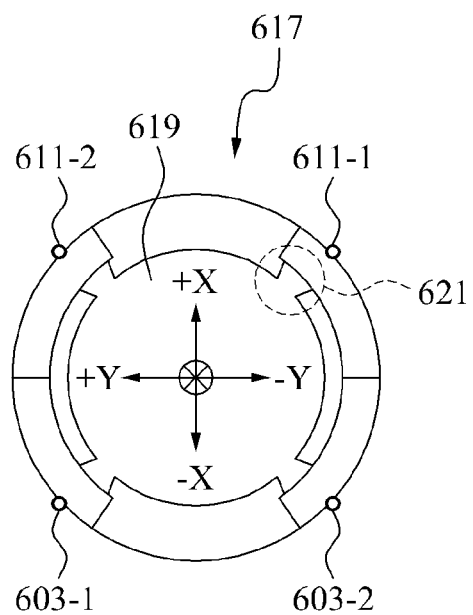
Figure 6C:
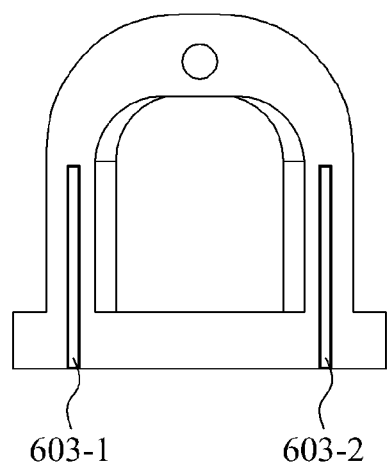
Figure 6D:
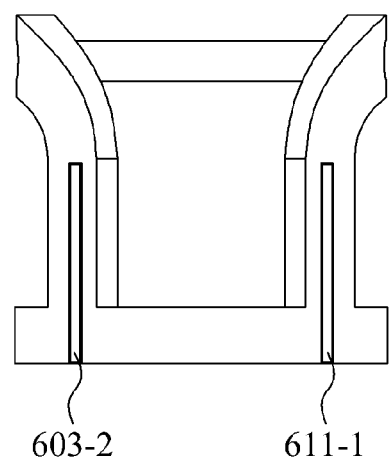

FIGS. 6A through 6D illustrate a body frame in a force sensing apparatus according to example embodiments. Here, FIG. 6A is a perspective view of the body frame. FIG. 6B is a top view of a bottom frame within the body frame. FIG. 6C is a side view of the body frame viewed from a first direction. FIG. 6D is a side view of the body frame viewed from a second direction.

Referring to FIGS. 6A through 6D, the force sensing apparatus may include a body frame 600 that may be disposed under a first grasper (not shown) and a second grasper (not shown) which may grip an object, and may be strained in at least one direction based on a strain signal associated with a strain of an object.

The body frame 600 may include two side frames, that is, a first side frame 601 and a second side frame 609, four sensing units 603-1, 603-2, 611-1, and 611-2 of a first group within the first side frame 601 and the second side frame 609, and a bottom frame 617.

For example, the first side frame 601 may include a first hole 605, and two support frames 607-1 and 607-2 that are formed on both sides of the first hole 605. The second side frame 609 may include a second hole 613, and two support frames 615-1 and 615-2 that are formed on both sides of the second hole 613.

Here, the first side frame 601 and the second side frame 609 may include a first connecting hole 623-1 and a second connecting hole 623-2 into which a drive shaft 625 is inserted, respectively. The drive shaft 625 may penetrate a first connection hole (not shown) of the first grasper and a second connection hole (not shown) of the second grasper within the force sensing apparatus. One side of the drive shaft 625 may be inserted into the first connecting hole 623-1 of the first side frame 601, and the other side of the drive shaft 625 may be inserted into the second connecting hole 623-2 of the second side frame 609, whereby the drive shaft 625 may connect the first grasper and the second grasper to the body frame 600.

The four sensing units 603-1, 603-2, 611-1, and 611-2 of the first group may be fixed to the two support frames 607-1 and 607-2 of the first side frame 601 and the two support frames 615-1 and 615-2 of the second side frame 609, respectively, and may sense a strain of the four support frames, as a whole. The strain may include, for example, a tensile strain or a compressive strain. Here, the four sensing units 603-1, 603-2, 611-1, and 611-2 of the first group may be disposed in the support frames 607-1, 607-2, 615-1, and 615-2. The support frames 607-1, 607-2, 615-1, and 615-2 may be positioned to correspond to grooves 621 formed at a number of portions of a bottom hole 619 within the bottom frame 617. Accordingly, cross-sectional areas of the support frames 607-1, 607-2, 615-1, and 615-2 may decrease, and stiffness of the support frames 607-1, 607-2, 615-1, and 615-2 may decrease as well, whereby the strain of the support frames 607-1, 607-2, 615-1, and 615-2 may be minutely sensed.

The bottom frame 617 may include the bottom hole 619, and the grooves 621. The bottom hole 619 may be disposed under, or at one end of, the first side frame 601 and the second side frame 609, and may be disposed to be perpendicular to the first hole 605 of the first side frame 601 and the second hole 613 of the second side frame 609. The grooves 621 may be formed at a number of portions of the bottom hole 619 to correspond to the support frames 607-1 and 607-2 of the first side frame 601 and the support frames 615-1 and 615-2 of the second side frame 609.

When the cross-sectional areas of the support frames 607-1, 607-2, 615-1, and 615-2 disposed to correspond to the grooves 621 decrease according to areas of the grooves 621, the stiffness of the support frames 607-1, 607-2, 615-1, and 615-2 may decrease and thus, the support frames 607-1, 607-2, 615-1, and 615-2 may be flexibly strained. Accordingly, the four sensing units 603-1, 603-2, 611-1, and 611-2 of the first group, each being fixed to the support frames 607-1, 607-2, 615-1, and 615-2, respectively, may minutely sense the strain of the support frames 607-1, 607-2, 615-1, and 615-2.

The force sensing apparatus may obtain information about a force applied to the object, based on data sensed by the four sensing units 603-1, 603-2, 611-1, and 611-2 of the first group. For example, the force sensing apparatus may obtain at least one of a direction and a magnitude of the force applied to the object, through the first grasper and the second grasper in the force sensing apparatus, using the strain of the support frames 607-1, 607-2, 615-1, and 615-2 in the first side frame 601 and the second side frame 609 into which the four sensing units 603-1, 603-2, 611-1, and 611-2 of the first group are inserted.

In particular, when the first sensing unit 603-1 and the second sensing unit 603-2 of the first group sense a compressive strain with respect to the first support frame 607-1 and the second support frame 607-2 of the first side frame 601, respectively, and the third sensing unit 611-1 and the fourth sensing unit 611-2 of the first group sense a tensile strain with respect to the third support frame 615-1 and the fourth support frame 615-2 of the second side frame 609, respectively, the force sensing apparatus may obtain a horizontal direction of the force applied to the object, for example, a direction of the force with respect to a −X axis, and a magnitude of the force that is proportional to the compressive strain or the tensile strain.

Conversely, when the first sensing unit 603-1 and the second sensing unit 603-2 of the first group sense a tensile strain with respect to the first support frame 607-1 and the second support frame 607-2 of the first side frame 601, respectively, and the third sensing unit 611-1 and the fourth sensing unit 611-2 of the first group sense a compressive strain with respect to the third support frame 615-1 and the fourth support frame 615-2 of the second side frame 609, respectively, the force sensing apparatus may obtain a horizontal direction of the force applied to the object, for example, a direction of the force with respect to a +X axis, and a magnitude of the force that is proportional to the compressive strain or the tensile strain.

In addition, when the second sensing unit 603-2 and the third sensing unit 611-1 of the first group sense a compressive strain with respect to the second support frame 607-2 of the first side frame 601 and the third support frame 615-1 of the second side frame 609, respectively, and the first sensing unit 603-1 and the fourth sensing unit 611-2 of the first group sense a tensile strain with respect to the first support frame 607-1 of the first side frame 601 and the fourth support frame 615-2 of the second side frame 609, respectively, the force sensing apparatus may obtain a horizontal direction of the force applied to the object, for example, a direction of the force with respect to a −Y axis, and a magnitude of the force that is proportional to the compressive strain or the tensile strain.

Conversely, when the second sensing unit 603-2 and the third sensing unit 611-1 of the first group sense a tensile strain with respect to the second support frame 607-2 of the first side frame 601 and the third support frame 615-1 of the second side frame 609, respectively, and the first sensing unit 603-1 and the fourth sensing unit 611-2 of the first group sense a compressive strain with respect to the first support frame 607-1 of the first side frame 601 and the fourth support frame 615-2 of the second side frame 609, respectively, the force sensing apparatus may obtain a horizontal direction of the force applied to the object, for example, a direction of the force with respect to a +Y axis, and a magnitude of the force that is proportional to the compressive strain or the tensile strain.

Further, when a tensile strain is sensed with respect to all of the support frames 607-1, 607-2, 615-1, and 615-2 in the first side frame 601 and the second side frame 609, the force sensing apparatus may obtain a vertical direction of the force applied to the object, for example, a direction of the force with respect to a +Z axis, and a magnitude of the force that is proportional to the tensile strain. Conversely, when a compressive strain is sensed with respect to all of the support frames 607-1, 607-2, 615-1, and 615-2 in the first side frame 601 and the second side frame 609, the force sensing apparatus may obtain a vertical direction of the force applied to the object, for example, a direction of the force with respect to a −Z axis, and a magnitude of the force that is proportional to the compressive strain.

Figure 7:
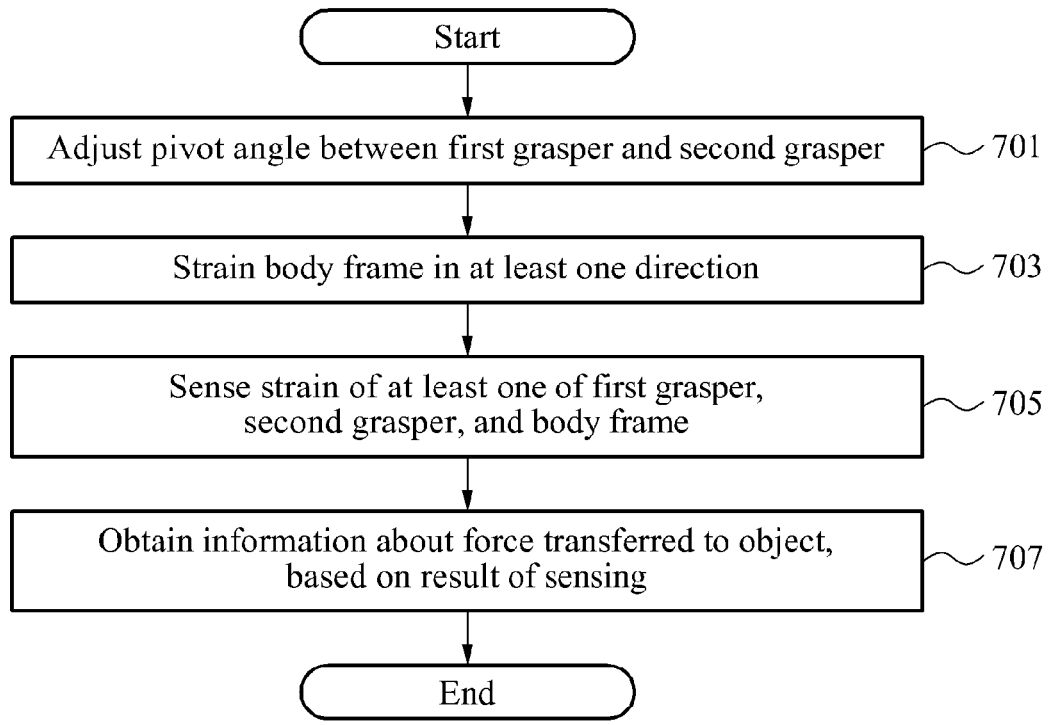
FIG. 7 illustrates an operating method of a force sensing apparatus according to example embodiments.

FIG. 7 illustrates an operating method of a force sensing apparatus according to example embodiments.

Referring to FIG. 7, in operation 701, the force sensing apparatus may receive an input of a grip signal associated with a grip of an object, and may adjust a pivot angle between a first grasper and a second grasper based on the input grip signal.

In operation 703, the force sensing apparatus may receive an input of a strain signal associated with a strain of the object, and may strain a body frame in at least one direction based on the input strain signal. Here, the body frame may include, for example, a first side frame including a number of support frames, among n support frames, and a second side frame including all remaining support frames, excluding the number of the support frames from the first side.

In operation 705, the force sensing apparatus may sense a strain, for example, a tensile strain or a compressive strain, with respect to at least one of the first grasper, the second grasper, and the support frames in the body frame.

The force sensing apparatus may sense a strain, for example, a tensile strain or a compressive strain, with respect to the first grasper and the second grasper, using two sensing units of a second group, each included in the first grasper and the second grasper, respectively. Here, each of the sensing units of the second group may correspond to, for example, an optical FBG or an optical strain gauge.

In addition, the force sensing apparatus may sense a strain, for example, a tensile strain or a compressive strain with respect to the n support frames, respectively, using n sensing units of a first group. Here, the n sensing units may be disposed in the support frames in the first side frame and the second side frame, respectively. Each of the n sensing units of the first group may correspond to, for example, an optical FBG or an optical strain gauge.

In operation 707, the force sensing apparatus may obtain information about a force transferred to the object associated with the n support frames, based on a result of the sensing, that is, data sensed by the n sensing units of the first group, and may output the obtained information through a display unit. Here, the information about the force transferred to the object may include, for example, information about a force applied to the object, and information about a force applied to grip the object.

In particular, the force sensing apparatus may obtain at least one of a direction and a magnitude of the force applied to the object, based on the data sensed by the n sensing units of the first group with respect to the compressive strain and the tensile strain of the n support frames.

For example, when the n sensing units of the first group sense a compressive strain with respect to the number of support frames, among the n support frames, for example, the support frames in the first side frame, and a tensile strain with respect to all the remaining support frames, excluding the number of the support frames from the first side, for example, the support frames in the second side frames, the force sensing apparatus may obtain a direction of a force applied to the object in a horizontal direction, and a magnitude of the force applied to the object in the horizontal direction.

In addition, when the n sensing units of the first group sense a compressive strain with respect to all of the n support frames, or when the n sensing units of the first group sense a tensile strain with respect to all of the n support frames, the force sensing apparatus may obtain at least one of a direction of a force applied to the object in a vertical direction, and a magnitude of the force applied to the object in the vertical direction.

Further, the force sensing apparatus may sense a compressive strain and a tensile strain of the first grasper and the second grasper, using sensing units of the second group, each being fixed to the first grasper and the second grasper, respectively, and may obtain at least one of information regarding whether the object is gripped, and a magnitude of the force applied to grip the object, based on the compressive strain and the tensile strain of the first grasper and the second grasper. For example, when the sensing units of the second group sense a tensile strain with respect to both the first grasper and the second grasper, the force sensing apparatus may determine that the object is being gripped with a magnitude of the force that is proportional to the tensile strain.

The method according to the above-described embodiments may be recorded in non-transitory computer-readable media including program instructions to implement various operations embodied by a computer. The media may also include, alone or in combination with the program instructions, data files, data structures, and the like. The program instructions recorded on the media may be those specially designed and constructed for the purposes of embodiments, or they may be of the kind well-known and available to those having skill in the computer software arts. Examples of non-transitory computer-readable media include magnetic media such as hard disks, floppy disks, and magnetic tape; optical media such as CD ROM discs and DVDs; magneto-optical media such as optical discs; and hardware devices that are specially configured to store and perform program instructions, such as read-only memory (ROM), random access memory (RAM), flash memory, and the like. The computer-readable media may also be a distributed network, so that the program instructions are stored and executed in a distributed fashion. The program instructions may be executed by one or more processors. The computer-readable media may also be embodied in at least one application specific integrated circuit (ASIC) or Field Programmable Gate Array (FPGA), which executes (processes like a processor) program instructions. Examples of program instructions include both machine code, such as produced by a compiler, and files containing higher level code that may be executed by the computer using an interpreter. The described hardware devices may be configured to act as one or more software modules in order to perform the operations of the above-described embodiments, or vice versa.

Although embodiments have been shown and described, it would be appreciated by those skilled in the art that changes may be made in these embodiments without departing from the principles and spirit of the disclosure, the scope of which is defined by the claims and their equivalents.

What is claimed is:

1. A force sensing apparatus, comprising:
a plurality of support frames configured to support a single surgical tool;
a plurality of support frame sensors, each sensor provided on each of the plurality of support frames, respectively, to sense a compressive strain and a tensile strain of each of the plurality of support frames;
a first grasper;
a second grasper;
an adjusting unit to adjust a pivot angle between the first grasper and the second grasper;
a first grasper sensor provided on the first grasper to sense a compressive strain and a tensile strain of the first grasper;
a second grasper sensor provided on the second grasper to sense a compressive strain and a tensile strain of the second grasper; and
a processor to obtain information about a force applied to an object by the plurality of support frames, based on data sensed by the plurality of support frame sensors and to obtain at least one of information regarding whether the object is gripped, and a magnitude of a force applied to grip the object, using a compressive strain and a tensile strain of the first grasper and the second grasper,
wherein, when the grasper sensors sense a tensile strain with respect to both the first grasper and the second grasper, the processor determines that the object is being gripped with a magnitude of a force that is proportional to the tensile strain.

2. The apparatus of claim 1, wherein the processor obtains at least one of a direction and a magnitude of the force applied to the object, based on the data sensed by the plurality of support frame sensors with respect to the compressive strain and the tensile strain of each of the plurality of support frames.

3. The apparatus of claim 1, wherein, when the plurality of support frame sensors sense a compressive strain with respect to a portion of the support frames, and a tensile strain with respect to the remaining portion of the support frames, the processor obtains at least one of a direction and a magnitude of a force applied to the object in a horizontal direction.

4. The apparatus of claim 1, wherein, when the plurality of support frame sensors sense a compressive strain with respect to all of the support frames, or when the plurality of support frame sensors sense a tensile strain with respect to all of the support frames, the processor obtains at least one of a direction and a magnitude of a force applied to the object in a vertical direction.

5. The apparatus of claim 1, further comprising:
a bottom frame disposed at one end of the plurality of support frames and perpendicular to the plurality of support frames,
wherein the bottom frame comprises:
a bottom hole; and
grooves formed at the bottom hole to correspond to the plurality of support frames.

6. The apparatus of claim 1, wherein a support frame sensor comprises an optical fiber Bragg grating.

7. The apparatus of claim 1, wherein a grasper sensor comprises an optical fiber Bragg grating.

8. The apparatus of claim 1, further comprising:
a drive shaft spanning the plurality of support frames from a first side to a second side, and connected to the first grasper and the second grasper.

9. A method of controlling a force sensing apparatus, the method comprising:
sensing a compressive strain and a tensile strain of each of a plurality of support frames, using a plurality of support frame sensors, each sensor provided on each of the plurality of support frames, respectively;
sensing a compressive strain and a tensile strain of a first grasper and a second grasper, using a first grasper sensor provided on the first grasper and a second grasper sensor provided on the second grasper;

obtaining information about a force applied to an object by the plurality of support frames, based on data sensed by the plurality of support frame sensors; and obtaining at least one of information regarding whether the object is gripped, and a magnitude of a force applied to grip the object, using the compressive strain and the tensile strain sensed by the grasper sensors, wherein the plurality of support frames is configured to support a single surgical tool, wherein the obtaining comprises determining that the object is being gripped with a magnitude of a force that is proportional to the tensile strain when the grasper sensors sense a tensile strain with respect to both the first grasper and the second grasper.

10. The method of claim 9, wherein the obtaining comprises obtaining at least one of a direction and a magnitude of the force applied to the object, based on the data sensed by the plurality of support frame sensors with respect to the compressive strain and the tensile strain of each of the plurality of support frames.

11. The method of claim 9, wherein the obtaining comprises obtaining at least one of a direction and a magnitude of a force applied to the object in a horizontal direction when the plurality of support frame sensors sense a compressive strain with respect to a portion of the support frames, and a tensile strain with respect to the remaining portion of the support frames.

12. The method of claim 9, wherein the obtaining comprises obtaining at least one of a direction and a magnitude of a force applied to the object in a vertical direction when the plurality of support frame sensors sense a compressive strain with respect to all of the support frames, or when the plurality of support frame sensors sense a tensile strain with respect to all of the support frames.

13. A non-transitory computer readable storage medium comprising executable instructions that, when executed by one or more processors, perform:

sensing a compressive strain and a tensile strain of each of a plurality of support frames, using a plurality of support frame sensors, each sensor provided on each of the plurality of support frames, respectively;

sensing a compressive strain and a tensile strain of a first grasper and a second grasper, using a first grasper sensor provided on the first grasper and a second grasper sensor provided on the second grasper;

obtaining information about a force applied to an object by the plurality of support frames, based on data sensed by the plurality of support frame sensors; and obtaining at least one of information regarding whether the object is gripped, and a magnitude of a force applied to grip the object, using the compressive strain and the tensile strain sensed by the grasper sensors, wherein the plurality of support frames is configured to support a single surgical tool, wherein the obtaining comprises determining that the object is being gripped with a magnitude of a force that is proportional to the tensile strain when the grasper sensors sense a tensile strain with respect to both the first grasper and the second grasper.

* * * * *